United States Patent [19]

Wright et al.

[11] Patent Number: 4,511,747
[45] Date of Patent: Apr. 16, 1985

[54] LIGHT OLEFIN CONVERSION TO HEAVIER HYDROCARBONS WITH SORPTION RECOVERY OF UNREACTED OLEFIN VAPOR

[75] Inventors: Bernard S. Wright, East Windsor; Chung H. Hsia, Matawan; Hartley Owen, Belle Mead, all of N.J.

[73] Assignee: Mobil Oil Corporation, New York, N.Y.

[21] Appl. No.: 576,179

[22] Filed: Feb. 1, 1984

[51] Int. Cl.³ ............................ C07C 3/02; C07C 3/03; C07C 3/20
[52] U.S. Cl. .................................. 585/415; 585/313; 585/314; 585/315; 585/329; 585/423; 585/424; 585/402; 585/533
[58] Field of Search ............... 585/313, 314, 315, 316, 585/415, 329, 423, 424, 402, 520

[56] References Cited

U.S. PATENT DOCUMENTS

| 3,827,968 | 8/1974 | Givens et al. | 585/322 |
| 4,433,185 | 2/1984 | Tabak | 585/312 |
| 4,450,311 | 5/1984 | Wright et al. | 585/413 |
| 4,456,779 | 6/1984 | Owen et al. | 585/415 |

Primary Examiner—Delbert E. Gantz
Assistant Examiner—A. Pal
Attorney, Agent, or Firm—A. J. McKillop; M. G. Gilman; L. G. Wise

[57] ABSTRACT

In the conversion of light olefins to heavier hydrocarbons, an improved recovery technique is provided for selectively removing unreacted light olefins from a catalytic reactor effluent. This system is useful in converting ethene-rich feedstocks to gasoline and/or distillate products, particularly in oligomerization processes employing shape selective siliceous catalysts such as ZSM-5 type zeolites. By recycling gasoline-range hydrocarbons as a sorbent liquid, unreacted $C_2^+$ components may be absorbed from reactor effluent vapor and returned for further contact with the catalyst.

8 Claims, 1 Drawing Figure

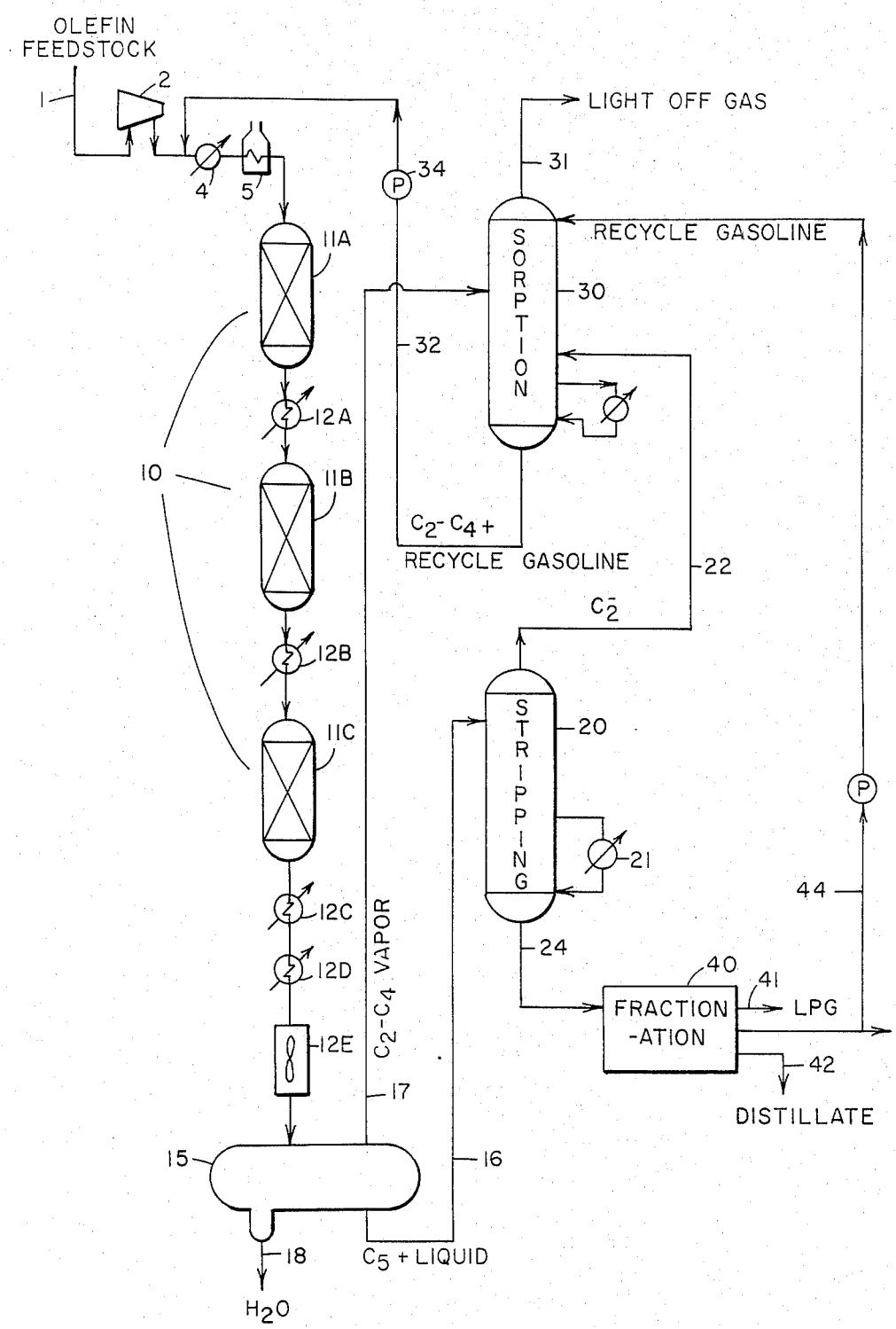

LIGHT OLEFIN CONVERSION TO HEAVIER HYDROCARBONS WITH SORPTION RECOVERY OF UNREACTED OLEFIN VAPOR

FIELD OF THE INVENTION

This invention relates to processes and apparatus for converting light olefins to higher hydrocarbons, such as gasoline-range and/or distillate-range fuels. In particular, it relates to techniques for operating a catalytic reactor system with ethene-rich feedstock and a unique effluent fractionation recovery system.

BACKGROUND OF THE INVENTION

Improved catalytic hydrocarbon conversion processes have created interest in utilizing olefinic feedstocks, such as petroleum refinery streams rich in lower olefins, for producing $C_5+$ gasoline, diesel fuel, etc. In addition to the basic work derived from ZSM-5 type zeolite catalyst research, a number of discoveries have contributed to the development of a new industrial process, known as Mobil Olefins to Gasoline/Distillate (MOGD). This process has significance as a safe, environmentally acceptable technique for utilizing refinery streams that contain lower olefins, especially $C_2-C_5$ alkenes. This process may supplant conventional alkylation units. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062; 4,211,640 and 4,227,992. The above-identified disclosures are incorporated herein by reference.

Conversion of lower olefins, especially propene and butenes, over H-ZSM-5 is effective at moderately elevated temperatures and pressures. The conversion products are sought as liquid fuels, especially the $C_5+$ aliphatic and aromatic hydrocarbons. Olefinic gasoline is produced in good yield by the MOGD process and may be recovered as a product or recycled to the reactor system for further conversion to distillate-range products.

As a consequence of the relatively low reactivity of ethene (ethylene) with known zeolite oligomerization catalysts prior distillate-mode reactor systems designed to completely convert a large ethylenic component of feedstock would require much larger size than comparable reactor systems for converting other lower olefins. However, under severe conditions of temperature and pressure, 75% or more of ethene can be converted in a single pass. Recycle of a major amount of ethene gas from the reactor effluent can result in significant increases in equipment size especially recycle compressors.

Olefinic feedstocks may be obtained from various sources, including fossil fuel processing streams, such as gas separation units, cracking of $C_2+$ hydrocarbons, coal byproducts, alcohol or ether conversion, and various synthetic fuel processing streams. Cracking of ethane and conversion of effluent is disclosed in U.S. Pat. No. 4,100,218 and conversion of ethane to aromatics over Ga-ZSM-5 is disclosed in U.S. Pat. No. 4,350,835. Olefinic effluent from fluidized catalytic cracking of gas oil or the like is a valuable source of olefins suitable for exothermic conversion according to the present MOGD process. It has been found that an olefin-oligomerization processing utilizing $C_2+$ olefinic feedstock can be operated to fractionate the effluent for ethene recovery. Accordingly, it is an object of the present invention to provide a unique effluent fractionation system for recovery of unreacted ethylene or the like for operation of an integrated MOGD type reactor system.

SUMMARY OF THE INVENTION

A novel technique has been found for separating and recycling lower olefin in a continuous catalytic process. Methods and apparatus are provided for converting light olefinic feedstock, especially gases comprising ethene, to heavier liquid hydrocarbon product. It is an object of this invention to effect conversion by a continuous technique for combining the feedstock stream with a liquid hydrocarbon stream containing a major amount of gasoline range hydrocarbons including $C_5+$ olefins; contacting the combined feedstock-gasoline stream at elevated temperature and pressure in a reaction zone with the shape selective medium pore zeolite oligomerization catalyst to convert at least a portion of the olefinic components to heavier hydrocarbons; cooling oligomerization reaction effluent to condense at least a portion of said heavier hydrocarbons; separating the cooled and partially condensed effluent stream into an ethene-rich vapor stream and condensed liquid hydrocarbon stream; fractionating said condensed hydrocarbons to provide a gasoline stream, a distillate product stream and a light hydrocarbon vapor stream containing unreacted ethene; contacting the ethene-rich vapor from the separation step and the light hydrocarbon vapor stream under sorption pressure conditions with a cooled liquid portion of the gasoline hydrocarbon to sorb ethene into the liquid gasoline stream; and pressurizing and recycling the sorbed ethene and gasoline stream for combining with an ethene-rich feedstock.

In a preferred embodiment, a continuous catalytic system is provided for converting ethene-rich olefinic feedstock to heavier hydrocarbons comprising reactor means for contacting the combined feedstock-gasoline stream at elevated temperature and pressure in a reaction zone with a shape selective medium pore zeolite oligomerization catalyst to convert at least a portion of olefinic components to heavier hydrocarbons, heat exchanger means for cooling oligomerization reaction effluent to condense at least a portion of said heavier hydrocarbons, means for separating the cooled and partially condensed effluent stream into an ethene-rich vapor stream and condensed liquid hydrocarbon stream, and fractionation means for distilling said condensed hydrocarbons to provide a gasoline stream, a distillate product stream and a light hydrocarbon vapor stream. The improved system comprises a means for contacting the ethene-rich vapor from the separating means and the light hydrocarbon vapor stream from the fractionation means under sorption pressure conditions with a cool liquid portion of the fractionated gasoline stream to sorb ethene into the liquid gasoline stream; and pump means for pressurizing and recycling the sorbed ethene and gasoline stream for combining with ethene-rich feedstock.

These and other objects and features of the novel MOGD system will be seen in the following description of the drawing.

DESCRIPTION OF THE DRAWING

The FIGURE is a process flow diagram showing relationships between the major unit operations.

DESCRIPTION OF PREFERRED EMBODIMENTS

An olefinic feedstock, such as $C_2$–$C_4$ olefins derived from alcohol dehydration or catalytic cracker (FCC) effluent, may be employed as a feedstock rich in ethene, propene, butenes, etc. for the process. Typically, the olefinic stock consists essentially of $C_2$–$C_6$ aliphatic hydrocarbons containing a major fraction of monoalkenes in the essential absence of dienes or other deleterious materials. The process may employ various volatile lower olefins as feedstock, with oligomerization of alpha-olefins being preferred for either gasoline or distillate production. Preferably the olefinic feedstream contains at least about 50 to 75 mole % $C_2$–$C_4$ alkenes.

Process conditions, catalysts and equipment suitable for use in the MOGD process are described in U.S. Pat. Nos. 3,960,978 (Givens et al), 4,021,502 (Plank et al), and 4,150,062 (Garwood et al). Hydrotreating and recycle of olefinic gasoline are disclosed in U.S. Pat. No. 4,211,640 (Garwood and Lee). Other pertinent disclosures include U.S. Pat. No. 4,227,992 (Garwood and Lee) and allowed U.S. patent application Ser. No. 508,907, filed 29 June 1983 (Wright et al.) relating to catalytic processes for converting olefins to gasoline/distillate. The above disclosures are incorporated herein by reference.

Catalyst

The catalytic reactions employed herein are conducted, preferably in the presence of medium pore shape selective silicaceous metal oxide crystalline catalysts, such as acid ZSM-5 type zeolites catalysts. These materials are commonly referred to as aluminosilicates or porotectosilicates; however, the acid function may be provided by other tetrahedrally coordinated metal oxide moieties, especially Ga, B, Fe or Cr. Commercially available aluminosilicates such as ZSM-5 are employed in the operative embodiments; however, it is understood that other silicaceous catalysts having similar pore size and acidic function may be used within the inventive concept.

The catalyst materials suitable for use herein are effective in oligomerizing lower olefins, especially ethene propene and butene-1 to higher hydrocarbons. The unique characteristics of the acid ZSM-5 catalyts are particularly suitable for use in the MOGD system. Effective catalysts include those zeolites disclosed in U.S. patent application Ser. No. 390,099 filed 21 June 1982 (Wong and LaPierre) and application Ser. No. 408,954 filed 17 Aug. 1982 (Koenig and Degnan), which relate to conversion of olefins over large pore zeolites. A preferred catalyst material for use herein is an extrudate (1–5 mm) comprising 65 weight % HZSM-5 and 35% alumina binder, having an acid cracking activity ($\alpha$) of about 160 to 200.

The members of the class of crystalline zeolites for use in this invention are characterized by a pore dimension greater than about 5 Angstroms, i.e., it is capable of sorbing paraffins having a single methyl branch as well as normal paraffins, and it has a silica to alumina mole ratio of at least 12.

Although such crystalline zeolites with a silica to alumina mole ratio of at least about 12 are useful, it is preferred to use zeolites having higher ratios of at least about 30. In some zeolites, the upper limit of silica to alumina mole ratio is unbounded, with values of 30,000 and greater.

The members of the class of zeolites for use herein are exemplified by ZSM-5, ZSM-5/ZSM-11 intermediate, ZMS-11, ZSM-12, ZSM-23, ZSM-35, ZSM-38, ZSM-48 and other similar materials. U.S. Pat. No. 3,702,886 describing and claiming ZSM-5 is incorporated herein by reference. Also, U.S. Pat. No. Re. 29,948 describing and claiming a crystalline material with an X-ray diffraction pattern of ZSM-5, is incorporated herein by reference as is U.S. Pat. No. 4,061,724 describing a high silica ZSM-5 referred to as "silicate" in such patent. The ZSM-5/ZSM-11 intermediate is described in U.S. Pat. No. 4,229,424. ZSM-11 is described in U.S. Pat. No. 3,709,979. ZSM-12 is described in U.S. Pat. No. 3,832,449. ZSM-23 is described in U.S. Pat. No. 4,076,842. ZSM-35 is described in U.S. Pat. No. 4,016,245. ZSM-38 is described in U.S. Pat. No. 4,046,859. The entire contents of the above identified patents are incorporated herein by reference. ZSM-48 is more particularly described in U.S. patent application Ser. No. 343,131 filed Jan. 27, 1982, the entire contents of which are incorporated herein by reference.

The zeolites used in additive catalysts in this invention may be in hydrogen form or they may be base exchanged or impregnated to contain a rare earth cation complement. Such rare earth cations comprise Sm, Nd, Pr, Ce and La. It is desirable to calcine the zeolite after base exchange.

The catalyst and separate additive composition for use in this invention may be prepared in various ways. They may be separately prepared in the form of particles such as pellets or extrudates, for example, and simply mixed in the required proportions. The particle size of the individual component particles may be quite small, for example from about 10 to about 150 microns, when intended for use in fluid bed operation, or may be as large as up to about 1–10 mm for fixed bed operation. The components may be mixed as powders and formed into pellets or extrudate, each pellet containing both components in substantially the required proportions. It is desirable to incorporate the zeolite component of the separate additive composition in a matrix. Such matrix is useful as a binder and imparts greater resistance to the catalyst for the severe temperature, pressure and velocity conditions encountered in many cracking processes. Matrix materials include both synthetic and natural substances. Such substances include clays, silica and/or metal oxides. The latter may be either naturally occurring or in the form of gelatinous precipitates, sols or gels including mixtures of silica and metal oxides. Frequently, zeolite materials have been incorporated into naturally occurring clays, e.g. bentonite and kaolin.

A particularly advantageous form of the catalyst is an extruded pellet having a diameter of about 1–3 mm, made by mixing steamed zeolite crystals eg. silica:alumina=70:1–500:1 with $\alpha$-alumina monohydrate in a proportion of about 2:1 and calcining the formed material to obtain an extrudate having a void fraction of about 30–40%, preferably about 36%.

General Process Description

Referring to the single FIGURE of the drawing, olefinic feedstock is supplied to the plant through fluid conduit 1 under steady stream conditions. This $C_2$+ feedstream is pressurized by compressor 2 and then sequentially heated by passing through process heat exchange unit 4 and furnace 5 to achieve the temperature for catalytic conversion in reactor system 10, including plural reactor vessels 11A, B, C, etc.

The reactor sub-system section shown consists of three downflow fixed bed, series reactors on line with heat exchanger cooling means 12 A, B, C, D, E between reactors and following the subsystem. The reactor configuration allows for any reactor to be in any position, A, B or C. The reactor in position A has the most aged catalyst and the reactor in position C has freshly regenerated catalyst. The cooled reactor effluent is first separated in a phase separator unit 15 to provide a condensed $C_5^+$ hydrocarbon liquid stream 16 and an ethene-rich vapor stream 17 comprising $C_2$–$C_4$ aliphatic hydrocarbons, along with any other unreacted gaseous components which might be present in the fedstock, such as hydrogen, carbon oxides, methane, nitrogen or other inert gases. Extraneous water may be removed from the system through separator line 18.

Condensed hydrocarbon reactor effluent 16 separated from the effluent vapor is further fractionated. A stripping unit 20 which may be heated by exchanging a reactor effluent stream reboiler 21, removes a significant fraction of dissolved light gases, including a minor amount of unreacted ethene. The $C_2^-$ stripped gases are passed through conduit 22 operatively connecting the stripper with a downstream sorption unit 30. Ethane and heavier hydrocarbons are removed from the recycle loop through stripper 20. This tower may be designed to lose as little ethylene as possible while maintaining a reasonable tower bottom temperature. High pressure favors the split between ethylene and ethane. Preferably the liquid stripper effluent 24 is debutanized in a fractionation subsystem 40 to provide a $C_4^-$ overhead stream, which is deethanized to provide LPG ($C_3$–$C_4$ alkane) product 41 and light offgas. The $C_5^+$ debutanizer bottom stream is split in an atmospheric distillation tower to provide raw distillate product stream 42 and an olefinic gasoline stream 44 for recycle and/or recovery of a minor amount as raw gasoline product. Details of a suitable fractionation system and other process conditions are disclosed in copending U.S. patent application Ser. No. 488,834 filed 26 Apr. 1983 (Owen et al), incorporated herein by reference.

To recycle unconverted ethylene, recycle gasoline is used to selectively absorb it in the ethylene absorber 30. Ethylene is recovered from the vapor stream 17 leaving the reactor effluent separator and from the stripper overhead 22. The $H_2$, CO, $CO_2$ and $CH_4$ inerts which may enter with the feed are removed in the tower overhead via conduit 31 to prevent their build up in the system.

The gasoline sorbent is an aliphatic hydrocarbon mixture boiling in the normal gasoline range of about 50° to 165° C. (125° to 330° F.), with minor amounts of $C_4$–$C_5$ alkanes and alkenes. Preferably, the total gasoline sorbent stream to ethylene sorbate mole ratio is greater than about 4:1. The process may be operated with a mole ratio of about 0.2 moles to about 10 moles of gasoline per mole of $C_2^+$ olefins in the feedstock.

The tower pressure and bottom temperature may be selected such that enough $CO_2$ leaves the system without carrying too much ethylene with it. Ethylene absorption efficiency can be improved if $CO_2$ is removed by an optional amine scrubber or the like (not shown) before entering the tower.

There is no need for a recycle compressor because all the recovered ethylene is dissolved in the recycle gasoline as a sorbate stream 32 and passed by pump 34 to the reactor. Advantageously, the liquid recycle stream is brought to process pressure before being heated to vaporize at least a portion of the olefinic components.

It is understood that the various process conditions are given for a continuous system operating at steady state, and that substantial variations in the process are possible within the inventive concept. In the detailed examples, metric units and parts by weight are employed unless otherwise specified.

The fractionation towers depicted in the drawing may employ a plate column in the primary tower and a packed column in the secondary tower, however, the fractionation equipment may also employ vapor-liquid contact means of various designs in each stage including packed beds of Raschig rings, saddles or other porous solids or low pressure drop valve trays (Glitsch grids). The number of theoretical stages will be determined by the feedstream composition, liquid:vapor (L/V) ratios, desired recovery and product purity.

Distillate Mode Reactor Operation

A typical distillate mode multi-zone reactor system employs inter-zone cooling, whereby the reaction exotherm can be carefully controlled to prevent excessive temperature above the normal moderate range of about 260° to 370° C.

Advantageously, the maximum temperature differential across any one reactor is about 30° C. ($\Delta T \sim 50°$ F.) and the space velocity (LHSV based on olefin feed) is about 0.5 to 1. Heat exchangers provide inter-reactor cooling and reduce the effluent to fractionation temperature. It is an important aspect of energy conservation in the MOGD system to utilize at least a portion of the reactor exotherm heat value by exchanging hot reactor effluent from one or more reactors with a fractionator stream to vaporize a liquid hydrocarbon distillation tower stream such as the debutanizer reboiler. Optional heat exchangers may recover heat from the effluent stream prior to fractionation. Gasoline from the recycle conduit is pressurized by pump means and combined with feedstock, preferably at a mole ratio of about 2–3 moles per mole of olefin in the feedstock. It is preferred to operate in the distillate mode at elevated pressure of about 4200 to 7000 kPa (600–1000 psig), with a minimum olefin partial pressure of 1200 kPa at the reactor system inlet.

The reactor system contains multiple downflow adiabatic catalytic zones in each reactor vessel. The liquid hourly space velocity (based on total fresh feedstock) is about 1 LHSV. In the distillate mode the molar recycle ratio for gasoline is at least equimolar, based on total olefins in the fresh feedstock and recycle.

The preferred molar ratio olefinic gasoline to fresh feedstock olefin is at least 2:1. This will also assure adequate sorbent for the sorption unit.

Typical reactor conditions are set forth in the following tables.

TABLE I

REACTOR SYSTEM CONVERSION
FEEDSTOCK AND YIELD

| Feedstock | | Yield on Olefin Converted | |
|---|---|---|---|
| Component | Wt % | Component | Wt % |
| Inerts | 5.00 | $CH_4$ | 0.10 |
| $CH^4$ | 2.00 | $C_2H_6$ | 3.90 |

TABLE I-continued

| | | | |
|---|---|---|---|
| $C_2H_4$ | 81.20 | $C_3H_8$ | 4.00 |
| $C_2H_6$ | 0.62 | $IC_4H_{10}$ | 2.00 |
| $C_3H_6$ | 3.71 | $NC_4H_{10}$ | 2.00 |
| $C_3H_8$ | 0.20 | $IC_5H_{12}$ | 1.32 |
| $IC_4H_{10}$ | 0.25 | $NC_5H_{12}$ | 0.09 |
| $NC_4H_{10}$ | 0.45 | $C_5H_{10}$ | 2.99 |
| $C_4H_8$ | 0.12 | $C_6$-300° Gaso. | 39.60 |
| $IC_5H_{12}$ | 2.31 | 330° + Dist. | 44.00 |
| $NC_5H_{12}$ | 0.10 | | |
| $C_5H_{10}$ | 1.73 | | |
| $C_6+$ | 2.31 | | |

| Conversion on Feed to Reactor | |
|---|---|
| Olefins | Wt. % |
| $C_2$ | 75 |
| $C_3$ | 95 |
| $C_4$ | 85 |

TABLE II

| REACTOR CONDTIONS | |
|---|---|
| Space Velocity, LHSV | 0.5 |
| (Based on olefins fed to reactor) | |
| Reactor A inlet pressure, psig | 900 |
| Minimum Olefin pp at reactor inlet, psia | 180 |
| Exothermic Heat of Reaction | 1040 |
| BTU/# olefins converted | |
| Rate of Heat Release | Uniformly over bed |
| Maximum Allowable | 50 |
| $\Delta T$ in Reactor, °F. | |
| Reactor Inlet Temperature | 500/700° F. |
| SOC/EOC | |
| Gasoline Recycle, Mol/Mol Olefin Feed | 2:1 |
| Coke on Catalyst, wt. % SOC | 0 |
| EOC | 30 |
| Cycle Length, Days | 30 |
| Catalyst | HZSM-5 |
| | 1/16" Extrudate |

More than 90% of ethylene is recovered in the above example from the effluent.

While the invention has been described by specific examples and embodiments, there is no intent to limit the inventive concept except as set forth in the following claims.

What is claimed is:

1. A continuous process for converting ethene-rich olefinic feedstock to heavier liquid hydrocarbons comprising the steps of
   combining the feedstock stream with a liquid hydrocarbon stream containing a major amount of gasoline range hydrocarbons including $C_5+$ olefins;
   contacting the combined feedstock-gasoline stream at elevated temperature and pressure in a reaction zone with the shape selective medium pore zeolite oligomerization catalyst to convert at least a portion of the olefinic components to heavier hydrocarbons;
   cooling oligomerization reaction effluent to condense at least a portion of said heavier hydrocarbons;
   separating the cooled and partially condensed effluent stream into an ethene-rich vapor stream and condensed liquid hydrocarbon stream;
   fractionating said condensed hydrocarbons to provide a gasoline stream, a distillate product stream and a light hydrocarbon vapor stream containing unreacted ethene;
   contacting the ethene-rich vapor from the separation step and the light hydrocarbon vapor stream under sorption pressure conditions with a cooled liquid portion of the gasoline hydrocarbon to sorb ethene into the liquid gasoline stream; and pressurizing and recycling the sorbed ethene and gasoline stream for combining with an ethene-rich feedstock.

2. The process of claim 1 wherein gasoline is recycled at a molar ratio of gasoline to fresh feedstock olefin of at least 2:1.

3. The process of claim 1 wherein the reaction zone contains acid ZSM-5 type catalyst.

4. The process of claims 1, 2 or 3 wherein the combined feedstock gasoline stream is heated to a temperature of about 260° C. to 370° C. and contacted with the oligomerization catalyst at a pressure of about 5000 to 7000 kPa with a minimum olefin partial pressure at reactor inlet of 1200 kPa.

5. The process of claim 3 wherein the feedstock space velocity is about 0.5 LHSV, based on total olefins contacted with the oligomerization catalyst.

6. A continuous process for converting light olefinic feedstock comprising $C_2+$ monolefinic by hydrocarbons to heavier hydrocarbons comprising the steps of
   combining said feedstock with a liquid hydrocarbon diluent stream containing a fraction of heavier hydrocarbons including $C_5+$ olefins;
   contacting the combined feedstock-diluent stream at elevated temperature and pressure in a reaction zone with the shape selective medium pore zeolite oligomerization catalyst to convert at least a portion of the olefinic components to heavier hydrocarbons;
   cooling oligomerization reaction effluent to condense at least a portion of said heavier hydrocarbons;
   separating the cooled and partially condensed effluent strem into a vapor stream comprising unreacted light olefin and condensed liquid hydrocarbon stream;
   fractionating said condensed liquid hydrocarbons to provide a recycle sorbent stream and at least one product hydrocarbon stream;
   contacting the vapor stream from the separation step and under sorption pressure conditions with cooled recycle sorbent to sorb said unreacted light olefin into the sorbent stream; and recycling the sorbent stream rich in olefin for further conversion with said olefinic feedstock.

7. The process of claim 6 wherein the combined feedstock gasoline stream is heated to a temperature of about 260° C. to 370° C. and contacted with the oligomerization catalyst comprising said ZSM-5 type zeolite at a pressure of about 5000 to 7000 kPa with a minimum olefin partial pressure at reactor inlet of 1200 kPa.

8. A continuous process for converting light olefinic feedstock comprising at least one monolefinic hydrocarbon to heavier hydrocarbons comprising the steps of
   combining said feedstock with a liquid hydrocarbon diluent stream containing heavier liquid hydrocarbons;
   contacting the combined feedstock-diluent stream at elevated temperature and pressure in a reaction zone with the shape selective medium pore zeolite oligomerization catalyst to convert at least a portion of the olefinic components to heavier hydrocarbons;
   cooling oligomerization reaction effluent to condense at least a portion of said heavier hydrocarbons;
   separating the cooled and partially condensed effluent stream into vapor stream and comprising unreacted light olefin and condensed liquid hydrocarbon stream;

fractionating said condensed liquid hydrocarbons to provide a recycle sorbent stream and at least one product hydrocarbon stream;

contacting the vapor stream from the separation step and under sorption pressure conditions with a cooled recycle sorbent to sorb said unreacted light olefin into the sorbent stream; and recycling the sorbent stream rich in olefin for further conversion with said olefinic feedstock.

* * * * *

UNITED STATES PATENT AND TRADEMARK OFFICE
CERTIFICATE OF CORRECTION

PATENT NO. : 4,511,747
DATED : April 16, 1985
INVENTOR(S) : Bernard S. Wright, Chung H. Hsia, Hartley Owen It is certified that error appears in the above-identified patent and that said Letters Patent is hereby corrected as shown below:

Col. 1, line 58, "fossile" should be --fossil--.

Col. 5, line 18, "fedstock," should be --feedstock,--.

Col. 5, line 25, after "stream" insert --in--.

Col. 8, line 18, delete "by".

Col. 8, line 32, "strem" should be --stream--.

Col. 8, line 33, after "and" insert --a--.

Signed and Sealed this

Twenty-seventh Day of August 1985

[SEAL]

Attest:

DONALD J. QUIGG

Attesting Officer

Acting Commissioner of Patents and Trademarks